(12) United States Patent
Davis

(10) Patent No.: US 9,139,694 B1
(45) Date of Patent: Sep. 22, 2015

(54) HIGH TEMPERATURE MATERIALS WITH LOW MOISTURE UPTAKE MADE FROM LICHEN METABOLITES

(71) Applicant: THE UNITED STATES OF AMERICA, AS REPRESENTED BY THE SECRETARY OF THE NAVY, Washington, DC (US)

(72) Inventor: Matthew C. Davis, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 101 days.

(21) Appl. No.: 13/894,684

(22) Filed: May 15, 2013

Related U.S. Application Data

(60) Provisional application No. 61/647,670, filed on May 16, 2012.

(51) Int. Cl.
C08G 64/00 (2006.01)
C08G 73/06 (2006.01)
C07C 263/00 (2006.01)

(52) U.S. Cl.
CPC ............ C08G 73/065 (2013.01); C07C 263/00 (2013.01)

(58) Field of Classification Search
CPC ... C07C 263/12; C07C 263/00; C08G 73/065
USPC ......................................................... 528/210
See application file for complete search history.

(56) References Cited

U.S. PATENT DOCUMENTS 5,627,222 A * 5/1997 Recker et al. .................. 523/400
8,853,343 B1 * 10/2014 Davis et al. .................... 528/210
2007/0116779 A1 * 5/2007 Mazzio .......................... 424/539

* cited by examiner

*Primary Examiner* — Shane Fang
(74) *Attorney, Agent, or Firm* — Charlene A. Haley

(57) ABSTRACT

A cured polycyanurate, thermoset resins, and methods of producing the same that will have both high thermal resistance as well as high hydrophobicity. Naturally occurring 5-alkylresorcinols and synthetic analogs can be made into cyanate ester. Composites made from these products will have greater durability against atmospheric water exposure. Applications include use in fiber-reinforced composite materials for lightweight, strong, and water-resistant aerospace components.

6 Claims, 2 Drawing Sheets

1 n = 0 resorcinol
2 n = 1 orcinol
3 n = 3 divarinol
4 n = 5 olivetol

HIGH TEMPERATURE MATERIALS WITH LOW MOISTURE UPTAKE MADE FROM LICHEN METABOLITES

CROSS-REFERENCE TO RELATED APPLICATIONS

This is a non-provisional patent application, claiming the benefit of, parent application Ser. No. 61/647,670 filed on May 16, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to cyanate ester, and more particularly, to using naturally occurring 5-alkylresorcinols and synthetic analogs to make cyanate ester.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DESCRIPTION OF EMBODIMENTS OF THE INVENTION

In embodiments of the invention, the cured polycyanurate will have both high thermal resistance as well as high hydrophobicity. Naturally occurring 5-alkylresorcinols and synthetic analogs can be made into cyanate ester. Composites made from these products will have greater durability against atmospheric water exposure. Applications include use in fiber-reinforced composite materials for lightweight, strong, and water-resistant aerospace components.

Cyanate esters are promising materials for thermosetting applications and can be strengthened by incorporation of fibers resulting in high thermal resistance and strong materials that are also lightweight. After curing, the polycyanurate has a propensity to absorb water which can cause volume changes as well as degrade the polymer network creating weakness and possibly crack promotion. The naturally occurring resorcinol derivatives with an alkane substituent at the 5-position are expected to have a greater degree of hydrophobicity in polycyanurate made from them. By incorporating these hydrophobic groups, the resulting composite parts will be much more durable and have a greater length of service time for aerospace components over the existing commercially available products of this class.

The naturally occurring 5-n-alkylresorcinols, resorcinolic lipids, were first identified from lichen extracts and later have been found in higher plants as well as certain animals, FIG. 1. These derivatives of resorcinol (1,3-dihydroxybenzene) can be used for the preparation of new materials using the rich polymer chemistry of diphenols already known. The resorcinolic lipids represent a source of chemical raw material that is an alternative to the ubiquitous petrochemical products and since they are derived from living organism, represent a renewable resource. In fact, many of these 5-n-alkylresorcinols would be rather complicated to manufacture starting from petrochemicals. The simplest molecules of this group, resorcinol and orcinol, have been used to make polymer materials, however the higher chain members have not. These longer chain phenolic lipids and polymers made from them, such as polycyanurate, will have a much great hydrophobicity and therefore greater resistance to water uptake.

Figure 1:
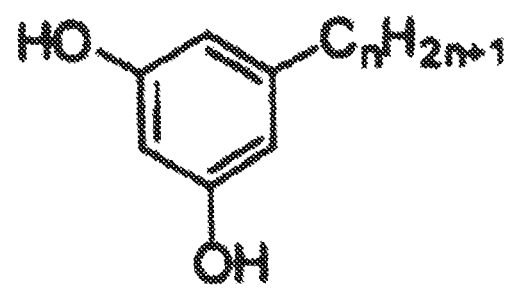
FIG. 1 is a chemical showing naturally occurring 5-n-alkylresorcinols, resorcinolic lipids, were first identified from lichen extracts and later have been found in higher plants as well as certain animals, according to embodiments of the invention.

FIG. 1. Naturally Occurring 5-n-alkylresorcinols.

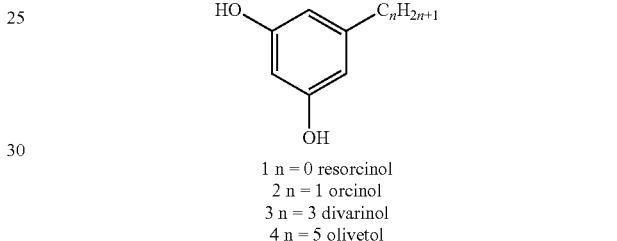

1 n = 0 resorcinol
2 n = 1 orcinol
3 n = 3 divarinol
4 n = 5 olivetol

It is water uptake, along with a exposure to heat, that can cause the breakdown of certain polymer systems, including polycyanurate. By appropriate selection of alkyl chain at the 5-position, the degree to which water uptake occurs can be controlled for the end-use material. Toughened composite materials made from the lipophilic phenols will be better for use in structural applications that are exposed to water, as they will be less likely to undergo volume expansion or water-promoted degradation. The two simplest members have been converted to dicyanate esters. By the addition of a single methyl group, orcinol dicyanate (ODiCy) has a melting point of 70° C. which is ten degree lower than resorcinol dicyanate (ResDiCy). (Grigat, E.: Putter, R. *Chem. Ber.* 1964,97, 3012-3017) The higher alkyl homologs are expected to have even lower melting points, or potentially liquids, which is significant to make the resulting dicyanate monomers easily processable in molding applications.

Some of the current theories of how lichen and higher plant biosynthesize these 5-n-alkylresorcinols is informative. Collie and Myers were the first to propose the idea that a class of natural products of plant origin were synthesized by putting together acetate units —CH 2—CO—) in a head-to-tail, repetitive fashion and called them 'ketides'. Birch and Donovan later built upon this idea that these polyketides could undergo cyclization by an aldol reaction to give phenolic natural products. (Collie J. N.; Myers, W. S. J. *Chem. Soc.* 1893, 63, 122. Birch A. J.; Donovan F. W. *Aus. J. Chem.* 1953, 6, 360.) The 5-n-alkylresorcinols are considered secondary metabolites, which mean that a primary metabolite undergoes further biochemical processing by the organism in the event of external stresses, such as environmental changes or biological attack. Through modern biochemical techniques, it has now been shown that the superfamily of enzymes known as polyketide synthases (PKSs), are responsible for the biosynthesis of 5-n-alkylresorcinols. Owing to the biosynthetic pathway shown in FIG. 2, it is clear why the alkyl chain of the naturally occurring resorcinolic lipids is only ever a methyl group, propyl, pentyl or other odd numbered methylene chain.

Figure 2:
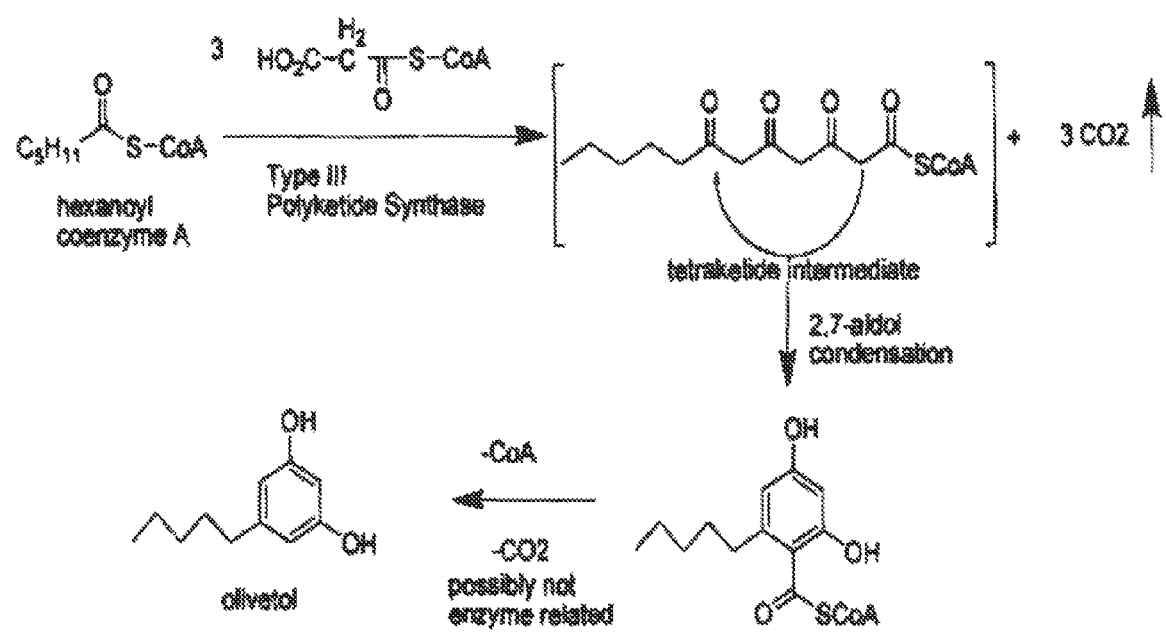
FIG. 2 is a flow diagram showing putative biosynthesis of phenolic lipids by lichen and plants, olivetol as an example, according to embodiments of the invention.

FIG. 2. Putative Biosynthesis of Phenolic Lipids by Lichen and Plants, Olivetol as an Example.

lyzing the combination of malonyl and alkanoyl co-enzyme A subunits. In the meantime, these phenolic lipids can be extracted and isolated from lichen and other plants and converted into thermosetting resins including cyanate ester and phenol-formaldehyde with water resistant properties.

Many unknown structures based on these phenolic lipids can also be synthesized through standard organic chemistry techniques, Scheme 1. Using chemistry discovered by Gilman, diprotected aresorcylic acid can be quickly converted

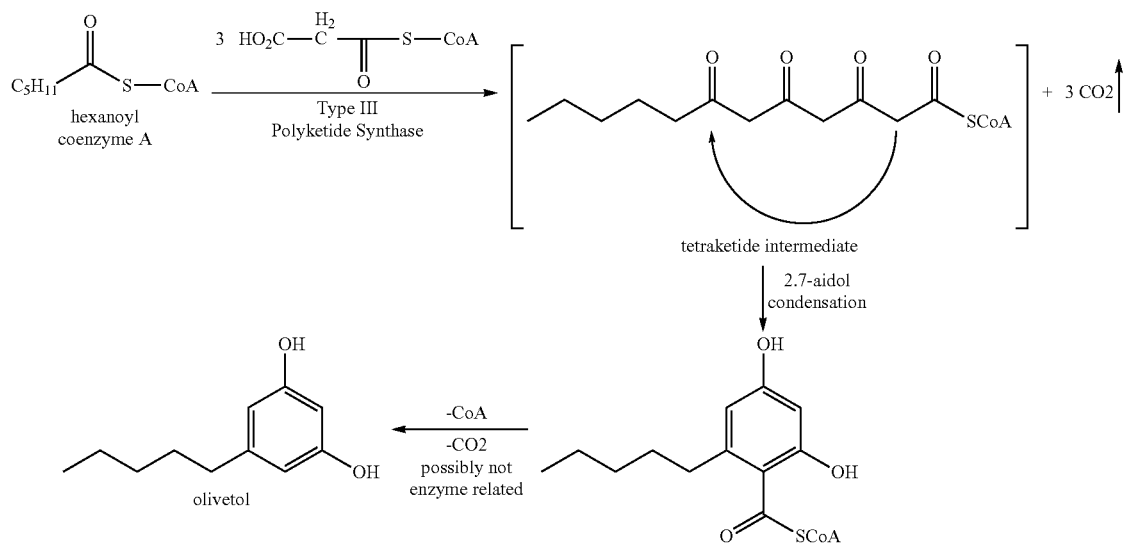

The understanding of the biochemistry whereby plants use carbon dioxide to build their wide variety of natural products is rapidly expanding. It is highly likely that in the future this power will be harnessed to allow for making any type of chemical structure desired using microorganisms as chemical factories. One can imagine growing a culture of microorganism in the presence of exogenous fatty acid or other carboxylic acid, and after incubation, isolating the designer resorcinol lipids. Or, expressing and harvesting the appropriate polyketide synthases to use in a cell-free preparation catalyzing into ketones using alkyllithium salts. The resulting ketone allows for a wide variety of chemical manipulations: reduction to the methylene; reaction with alkyllithium and reduction to tertiary alkane; reaction with fluorinating reagents to gem-difluoro compounds.

Scheme 1. Chemical Synthesis of New Derivatives of Phenolic Lipids.

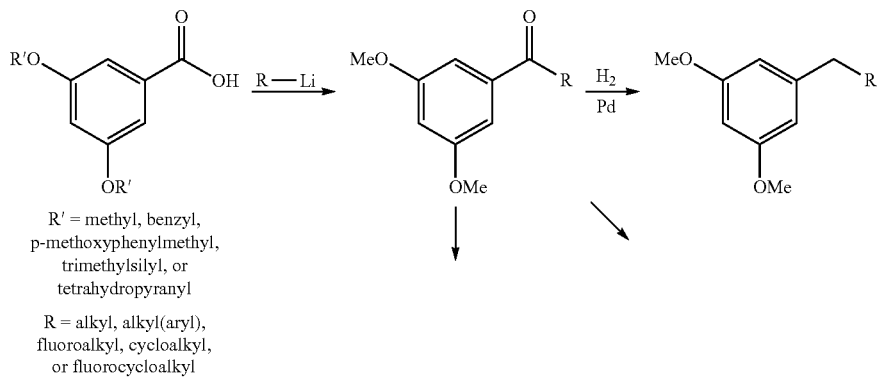

-continued

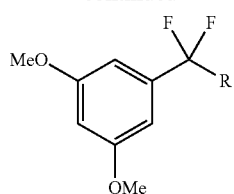

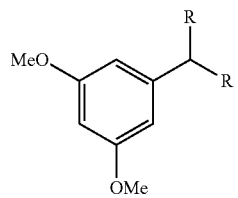

The protected phenolic lipids can then be deprotected to give the 5-substituted-resorcinols which are the monomer starting materials for polymer synthesis, Scheme 2. Two polymer systems currently of interest are cyanate ester and phenol-formaldehyde-type. These are both thermosetting materials that can undergo polymerization induced simply with heat.

Scheme 2. Deprotection and Synthesis of Polymers.

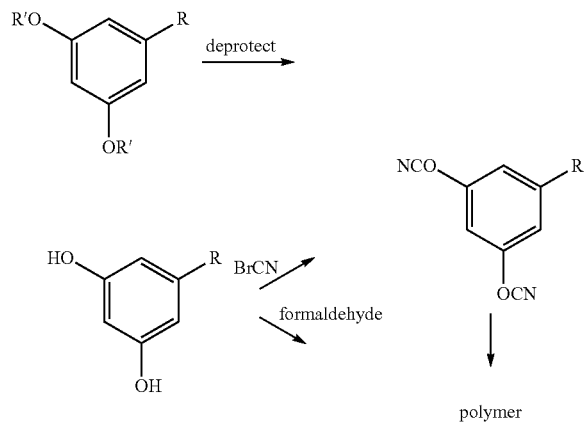

R' = methyl, benzyl, p-methoxyphenylmethyl, trimethylsilyl, or tetrahydropyranyl
R = alkyl, alkyl(aryl), fluoroalkyl, cycloalkyl, or fluorocycloalkyl Of the two simplest dicyanates that have already been made, ResDiCy is the best studied with a melting point of 80° C. and a glass transition temperature (Tg) for its polycyanurate network of 275° C. (Hergenrother, P. M., Harrison, E. S., Gosnell, R. B. 20th Nat. SAMPE Symp. Expos. 1975, 20, 243.) The high thermal stability of its polycyanurate makes this monomer attractive for heat stressed application in aerospace technology, such as rocket engine componentry. It is acknowledged that while a long chain hydrocarbon added at the 5-position will enhance hydrophobicity, it may have a detrimental impact on the thermal stability (lower Tg) of the resulting polycyanurate. For example, OrDiCy with an additional methyl group has a melting point to 70° C., thermogravimetric analysis of its polycyanurate, however, is unknown. Some hydrocarbon substituents may in fact improve heat resistance and water resistance, for example adamantyl or cyclohexyl analogs. By making a series of dicyanate derivatives of resorcinolic lipids and studying the thermal properties of the cured resins, it is likely that an analog will be found with high resistance to water uptake and only a small decrease in thermal strength.

Process for making cyanate esters, including: isolate resorcinolic lipids from lichen and other plants, synthesize new resorcinolic lipids, convert resorcinolic lipids into resorcinolic dicyanate ester lipids, cure dicyanate ester lipids into a molded lipophilic polycyanurate part, and/or assemble parts into a water resistant aerospace component.

Resorcinolic lipids

Water-resistant polycyanurate network

R=alkane, cycloalkane, perfluoroalkane, perfluorocycloalkane, alkylaryl, aryl, fluoroaryl, trialkylsilyl, and/or triarylsilyl.

Embodiments of the invention generally relate to processes for making thermoset resins and thermoplastics including, isolating resorcinolic lipids from plant and/or animal sources having 5-n-alkylresorcinols

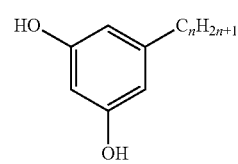

wherein the 'n' is selected from the group consisting of n=0 being resorcinol, n=1 being orcinol, n=3 being divarinol, and n=5 being olivetol, and converting the resorcinolic lipids into resorcinolic dicyanate ester lipids. Another aspect of the invention generally relate to processes for making thermoset resins and thermoplastics including, isolating resorcinolic lipids from plant and/or animal sources and converting the resorcinolic lipids into resorcinolic dicyanate ester lipids.

Embodiments further include curing the resorcinolic dicyanate ester lipids with heat to produce thermoset resins including epoxies, cyanate esters, phenolic, and thermoplastics. Other embodiments further include curing the resorcinolic dicyanate ester lipids with heat and a suitable catalyst to produce thermoset resins including epoxies, cyanate esters, phenolic, and thermoplastics. These compounds can be cured either with or without a catalyst. Catalysts are typically based on transition metal (Co, Ni, etc.) compounds. In regard to temperature, a broad range—from ambient to 350 degrees C. for curing. Catalyst concentration ranges from about 0.001% to 15% by weight. In embodiments, 0-2 mol % of catalyst loading would cover any cure protocol. A catalyst is not needed simply to provide thermal cure. Catalysts (example: co-ordination complexes of Na, Mg, Al, K, Ca, Sc, Ti, V, Cr, Mn, Fe, Co, Ni, Cu, Zn, Sr, Ag, Sn, Ba, Au with naphteanate, acetylacetonate, and the like; organic amine, imidazoles, iminocarbonates, traizines, phenols, and other proton sources, halide salts of Ti, Fe, Cl, and surfaces including acidic groups such as silanol and carboxylic acid) may be added to achieve more rapid cure at a given temperature.

Still yet other embodiments further include molding the thermoset resins and thermoplastics in a component to protect against extreme heat and moisture. Yet other embodiments further include coating a component with the thermoset resins and thermoplastics to protect against extreme heat and moisture. In embodiments, the components are for aerospace application. Other aspects of the invention generally relate to thermoset resins and thermoplastics produced by the processes herein. In other embodiments, hydrophobic dicyanate ester resins or dicyanate ester resins with low water uptake with less than ~1.5% water uptake after 96 hours in 85 degree C. water are unique. Also a variety of structural variations including fluorinated versions could be considered both hydrophobic and lipophobic. Embodiments of the invention should cover all the R and R' groups specified in the scheme herein.

The term "converting" covers both "synthesizing" and other forms of "converting" that might not be considered identical to synthesis (e.g. synthesis followed by separation and melting, or, on the extremely unlikely side, non-synthetic conversions, e.g. cyanogen halide ion implantation). 5-n-alkylresorcinols are examples of resorcinolic lipids. "5-n-alkylresorcinols" would refer to resorcinol having C-sub-n-H-sub-(2n+1) attached at the 5-position. It is understood that "resorcinolic lipids" are to include any molecular in which a resorcinol fragment (lacking one —H) is attached to a hydrocarbon fragment, with the attachment being possible at the 2, 4, or 5 position.

Embodiments further include hydrophobic dicyanate ester resins or dicyanate ester resins with low water uptake (in embodiments, probably less than ~1.5% water uptake after 96 hours in 85 degree C. water). Also embodiments include a variety of structural variations including fluorinated versions which could be considered both hydrophobic and lipophobic. Embodiments of the invention should cover all the R and R' groups specified in the scheme herein. Embodiments of the invention can be cured either with or without a catalyst. Catalysts are typically based on transition metal (Co, Ni, etc.) compounds. Embodiments of the invention include dicyanate esters that are synthesized as described in the specification herein. In embodiments, the pure resins are then "converted" to polycyanurates with the application of heat and/or a catalyst.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for making thermoset resins and thermoplastics, comprising:
   isolating resorcinolic lipids from plant and/or animal sources having 5-n-alkylresorcinols

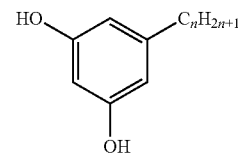

wherein said 'n' is selected from the group consisting of n=1 being orcinol, n=3 being divarinol, and n=5 being olivetol; and
   converting said 5-alkyl resorcinolic lipids into 5-alkyl resorcinolic dicyanate ester lipids.

2. The process according to claim 1, further comprising curing said resorcinolic dicyanate ester lipids with heat to produce thermoset resins including epoxies, cyanate esters, phenolic, and thermoplastics.

3. The process according to claim 1, further comprising curing said resorcinolic dicyanate ester lipids with heat and a suitable catalyst to produce thermoset resins including epoxies, cyanate esters, phenolic, and thermoplastics.

4. A process for making thermoset resins and thermoplastics, comprising:
   isolating 5-alkyl resorcinolic lipids from plant and/or animal sources; and
   converting said 5-alkyl resorcinolic lipids into 5-alkyl resorcinolic dicyanate ester lipids.

5. The process according to claim 4, further comprising curing said 5-alkyl resorcinolic dicyanate ester lipids with heat to produce thermoset resins including epoxies, cyanate esters, phenolic, and thermoplastics.

6. The process according to claim 4, further comprising curing said 5-alkyl resorcinolic dicyanate ester lipids with heat and a suitable catalyst to produce thermoset resins, epoxies, cyanate esters, phenolic, and thermoplastics.

* * * * *